(12) United States Patent
Fan et al.

(10) Patent No.: US 7,297,338 B2
(45) Date of Patent: Nov. 20, 2007

(54) **AVIAN VACCINE COMPOSITION FOR THE PROTECTION OF POULTRY AGAINST DISEASE AND INFECTION CAUSED BY *E. COLI* AND *SALMONELLA***

(75) Inventors: Henry H. Fan, Hickory, NC (US); Mahesh Kumar, Fort Dodge, IA (US)

(73) Assignee: Wyeth, Madison, NJ (US)

( * ) Notice: Subject to any disclaimer, the term of this patent is extended or adjusted under 35 U.S.C. 154(b) by 236 days.

(21) Appl. No.: 10/837,810

(22) Filed: May 3, 2004

(65) Prior Publication Data
US 2004/0234550 A1 Nov. 25, 2004

Related U.S. Application Data

(60) Provisional application No. 60/470,470, filed on May 14, 2003.

(51) Int. Cl.
*A61K 39/116* (2006.01)
(52) U.S. Cl. .............................. 424/203.1; 424/234.1; 424/257.1; 424/243; 424/252.3; 424/258.1; 435/243; 435/172.1
(58) Field of Classification Search ............ 424/234.1, 424/257.1, 243, 252.3, 258.1, 203.1; 435/243, 435/172.1
See application file for complete search history.

(56) References Cited

U.S. PATENT DOCUMENTS 5,851,519 A * 12/1998 Dougan et al. ............ 424/93.2
6,231,871 B1    5/2001 Coloe
6,902,906 B1 *  6/2005 Chatfield ..................... 435/41

FOREIGN PATENT DOCUMENTS

EP    0 400 958 A2    12/1990
EP    0 650 733 A1    5/1995

OTHER PUBLICATIONS

Gerard L. Cooper, et al., "Vaccination of chickens with *Salmonella enteritidis* aroA live oral salmonella vaccine," Microbial Pathogenesis, 1990, vol. 9, pp. 255-265.

J.O. Hassan, et al., "Control of Colonization by Virulent *Salmonella typhimurium* by Oral Immunization of chickens with Avirulent Δcya Δcrp *S. typhimurium*," Res. Microbiol., 1990, vol. 141, pp. 839-850.

Lei Wang, et al, "Immunization of mice wtth live oral vaccine based on a *Salmonella enterica* (sv Typhimurium) aroA strain expressing the *Escherichia coli* O111 0 antigen"/ Microbial Pathogenesis 1999; 27: 55-59.

"Safety, Immunogenicity, and Efficacy of Two *Escherichia coli* cyp crp Mutants as Vaccines for Broilers". Avian Diseases 46:287-297, 2002.

* cited by examiner

*Primary Examiner*—Jennifer Graser

(57) ABSTRACT

There is provided a vaccine composition comprising a combination of a genetic deletion mutant *S. typhimurium* microorganism and a genetic deletion mutant *E. coli* microorganism, suitable for mass application to poultry. Also provided is a safe and effective method to protect poultry against the ravages of *E. coli* and *Salmonella* infection and disease.

15 Claims, No Drawings

AVIAN VACCINE COMPOSITION FOR THE PROTECTION OF POULTRY AGAINST DISEASE AND INFECTION CAUSED BY E. COLI AND SALMONELLA

This application claims priority from copending provisional Application Ser. No. 60/470,470, filed May 14, 2003, the entire disclosure of which is hereby incorporated herein by reference.

FIELD OF THE INVENTION

The present invention relates to combination avian vaccines against *Salmonella* and *E. coli* infections. In particular, the invention is directed to a vaccine composition for poultry containing a mutant live, attenuated strain, respectively, of *Salmonella* and *E. coli*. The invention also relates to a method of preventing bacterial disease in poultry, including chickens, by administering a vaccine containing attenuated microorganisms of *Salmonella* and *E. coli*.

BACKGROUND OF THE INVENTION

In the poultry industry, newly hatched chicks are particularly susceptible to *Salmonella* infection. This bacterium is spread from fecal material, and young animals can become infected from the soil or perhaps from contaminated processed feed, leading to a high mortality rate and concomitant serious economic consequences. In addition to *Salmonella*, the poultry house environment also maintains large numbers of *Escherichia coli* (*E. coli*) through fecal contamination, leading to systemic infection in the poultry via the respiratory tract and intestines. This *E. coli* infection is referred to as colibacillosis. The resultant bacteremia progresses to septicemia and death, or the infection extends to serosal surfaces, pericardium, joints and other organs. Both *E. coli* and *Salmonella* diseases therefore present a serious threat to the poultry industry on a continuing basis.

Treatment and prevention strategies against *Salmonella* include in ovo vaccination against *Salmonellosis*, such as that described in U.S. Pat. No. 6,231,871 B1. However, in ovo vaccination can be arduous in large poultry facilities. Many hatcheries lack the sophisticated and specialized egg-vaccinating equipment which is necessary. Regarding *E. coli* infection, control of predisposing infections or environmental factors and early use of antibiotics is an accepted practice to minimize *E. coli* presence in poultry houses. Unfortunately, a high frequency of resistance to tetracycline, kanamycin, neomycin, cephalotin, streptomycin and erythromycin has been observed.

Although there is a commercial live *E. coli* vaccine available for use against colibacillosis in turkeys, there does not appear to be a fully suitable vaccine for use in chickens. Moreover, there appears to be no combination vaccine composition available for protection against both *Salmonella* and *E. coli* infections that is safe and effective for poultry, including chickens, and that is suitable for economic administration such as mass application to post-hatch birds via spray or drinking water.

Therefore, it is an object of this invention to provide a safe and effective vaccine composition against infection and disease caused by *Salmonella* species, including *Salmonella typhimurium*, as well as against *Escherichia coli*, in poultry, including chickens.

It is another object of this invention to provide a method for the prevention or amelioration of infection or disease caused by *Salmonella* species (including *S. typhimurium*, as well as others such as *S. enteritidis* and *S. heidelberg*), and by *E. coli* in poultry.

It is a feature of this invention that the vaccine composition is suitable for mass application, such as via drinking water or spraying.

It is an advantage of this invention that the live vaccine composition provide both cellular and humoral immunity responses in the host.

SUMMARY OF THE INVENTION

The present invention provides a safe and effective avian vaccine composition which comprises an immunogenically effective amount of a combination of an *Escherichia coli* genetic deletion mutant microorganism and a *Salmonella typhimurium* genetic deletion mutant microorganism and a pharmacologically acceptable carrier.

The present invention also provides a method for the prevention or amelioration of *E. coli* and *Salmonella* infection or disease in poultry which comprises administering to said poultry an immunogenically effective amount of a combination of an *Escherichia coli* genetic deletion mutant microorganism and a *Salmonella typhimurium* genetic deletion mutant microorganism.

Other objects and features of the invention will become more apparent from the detailed description set forth herein below.

DETAILED DESCRIPTION OF THE INVENTION

Avian colibacillosis in domestic poultry is frequently associated with *Escherichia coli* (*E. coli*), including serotypes O78, O1, O2, as well as some especially virulent untyped strains. Infection commonly occurs via the respiratory tract, often following exposure to, or infection by, other poultry community diseases. In chickens, colibacillosis generally affects broilers between 3 to 10 weeks of age and is associated with high morbidity and mortality. The most severe manifestation of avian colibacillosis is septicemia which is characterized by pericarditis, perihepatitis and airsacculitis. Other problems include arthritis and cellulitis. Isolates of *E. coli* from poultry are frequently resistant to drugs such as ampicillin, chloramphenicol, oxytetracycline, neomycin, gentamicin, nitrofurans, nalidixic acid, polymixin B, sulfonamides, or the like. However, the *E. coli* aroA genetic deletion mutant microorganism, *E. coli* aroA-, having the identifying characteristics of the strain deposited with the American Type Culture Collection (ATCC) at 10801 University Boulevard, Manassas, Va. 20110 USA on Mar. 27, 2003 and having ATCC accession number PTA-5094, is safe and effective for use in a vaccine against avian colibacillosis in poultry, including chickens. The *E. coli* aroA- PTA-5094 vaccine immunogen, when administered to chickens, provides good cellular and humoral immune responses. Further, said vaccine may be easily produced and may be administered via mass application, i.e. spray or drinking water. The *E. coli* aroA- PTA-5094 vaccine and the construction thereof is also described in co-pending patent application Ser. No. 60/470,471 filed concurrently herewith and incorporated herein by reference thereto. In addition, the invention further contemplates other live, attenuated *E. coli* gene mutants, including deletion mutants, in particular aroA deletion mutants, as immunogens as part of a combination vaccine herein described.

Another significant source of infection in domestic poultry is from *Salmonella* bacteria, including *Salmonella typhimurium* (*S. typhimurium*). Newly hatched birds are particularly susceptible to *Salmonella* infection, and a high mortality rate as a result thereof immediately post-hatching can have serious economic consequences. Many species of *Salmonella* also cause infection in humans and other animals, making control of *Salmonella* infection in poultry of particular importance. Live attenuated *Salmonella* vaccines have been shown to protect chickens (Cooper, et al., *Microb. Pathog.*, 9:255-265, 1990; Hassan and Curtis III, *Res. Microbial.*, 141:839-950, 1990). Importantly, the avirulent *S. typhimurium* aroA deletion mutant microorganism having the identifying characteristics of *S. typhimurium* STM-1 deposited at the Australian Government Analytical Laboratories under Accession Number N93/43266 has been found to be particularly effective in protecting poultry against *Salmonella* infection and disease. Said *S. Typhimurium* STM-1 microorganism and the construction thereof is described in U.S. Pat. No. 6,231,871, which is incorporated herein by reference. In addition, the invention further contemplates other live, attenuated *Salmonella* gene mutants, including deletion mutants, in particular aroA deletion mutants, as immunogens as part of a combination vaccine herein described.

Since in ovo and oral vaccination routes such as gavage may be arduous and inconvenient, a vaccine composition suitable for mass application via spray or drinking water would be highly preferred. Similarly, a single combination vaccine composition which would be safe and effective against both *E. coli* and *Salmonella* infection and disease in poultry would be particularly preferred. However, any time more than one organism is assembled into a single vaccine composition, interference may occur such that the immune response is not as great as when the individual organism has been administered separately. Therefore, a vaccine composition comprising a combination of more than one microorganism cannot, on the face of it, be predicted to elicit the desired effect and may actually be less efficacious than the administration of each microorganism individually.

Surprisingly, it has now been found that a vaccine composition which comprises: an immunogenically effective amount of a combination of an *E. coli* genetic deletion mutant microorganism and a *S. typhimurium* genetic deletion mutant microorganism; and a pharmacologically acceptable carrier is safe and effective for the protection of poultry against disease and infection caused by *Salmonella* and *E. coli*. Advantageously, the composition of the invention comprises live avirulent attenuated microorganisms as immunogens capable of inducing both cellular and humoral immunity responses in the host, while demonstrating safety even when administered via the respiratory system. This inherent safety allows for economic and efficient mass application routes such as spray (e.g. coarse spray) or drinking water, or both, even at very young ages. This feature is important since administration of two bacterial immunogens via the respiratory mucosae of young birds would otherwise be expected to have a considerable deleterious effect on the animals.

Immunogenically effective amounts of the respective microorganisms in the combination vaccine may vary according to the age and size of the host, the severity of the infection, the virility of the pathogen, the mode of administration or the like. In general, suitable effect amounts per dosage unit may be about $10^2$ to $10^4$ colony forming units (cfu), preferably about $5.0\times10^2$ cfu to $5.0\times10^{10}$ cfu, more preferably about $3.0\times10^6$ cfu to $6.0\times10^6$ cfu of the *E. coli* genetic deletion mutant microorganism and about $10^2$ to $10^{14}$ cfu, preferably about $5.0\times10^2$ to $5.0\times10^{10}$ cfu, more preferably about $2.0\times10^6$ to $6.0\times10^6$ cfu of the *S. typhimurium* genetic deletion mutant microorganism.

One or two dosage units may be contemplated by the skilled artisan. If two dosage units are selected, then vaccination is typically effected at about day 1 post-hatch and again at about one to two weeks of age. A dosage unit is desirably about 0.5 to 1 mL of vaccine per bird, but that quantity may be optimized to deliver an immunogenically effective amount of the respective microorganism hereinabove described.

The *E. coli* and *S. typhimurium* genetic deletion mutant microorganisms suitable for use in the composition of the invention may be an *E. coli* or *S. typhimurium* microorganism which has been modified by inducing a mutation in a biosynthetic pathway of an amino acid or vitamin or other essential molecule; preferably the mutation affects the biosynthesis of one or more of the amino acids selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine; more preferably by inducing a mutation in an aromatic vitamin biosynthetic pathway; particularly preferably by inducing a mutation in the aropathway, more particularly in the aroA gene. Specific examples of the preferred *E. coli* and *S. typhimurium* genetic deletion mutant microorganisms are, respectively, the *Escherichia coli* aroA-microorganism deposited at the American Type Culture Collection on Mar. 27, 2003 and assigned number PTA-5094, hereinafter designated as *E. coli* aroA- PTA-5094 and *Salmonella typhimurium* strain STM-1, deposited at the Australian Government Analytical Laboratories under Accession Number N93/43266, hereinafter designated as *S. typhimurium* STM-1.

The genetic deletion mutant microorganisms as part of the vaccine of the invention may be serially passaged using media and techniques available to the skilled artisan. Serial passaging can serve to further attenuate the strain to make it more suitable as a vaccine immunogen. Up to about 10 serial passages are contemplated, with about 3 to 5 being preferred.

Pharmacologically acceptable carriers suitable for use in the vaccine composition of the invention may be any conventional liquid carrier suitable for veterinary pharmaceutical compositions, preferably a balanced salt solution suitable for use in tissue or cell culture media such as sterile phosphate buffered saline, more preferably distilled water. Other suitable media can include emulsions. The vaccine of the invention may also be adjuvanted by the skilled technician. When application of the vaccine is via drinking water, non-fat dry milk may be utilized as a carrier. The non-fat dry milk appears to stabilize the vaccine, and perhaps neutralizes the action of some trace minerals that can affect viability.

In actual practice, the *E. coli* genetic deletion mutant microorganism may be combined with the *S. typhimurium* genetic deletion mutant microorganism and the combined microorganisms may be admixed with a liquid carrier and administered as a spray or drinking water additive. Alternatively, each individual microorganism may be admixed with a liquid carrier and then combined together for administration as a spray or drinking water additive, or may be administered simultaneously.

Accordingly, the present invention also provides a method for the prevention or amelioration of *E. coli* and *Salmonella* infection or disease in poultry which comprises administering to said poultry an immunogenically effective amount of a combination of an *E. coli* genetic deletion mutant microorganism and a *S. typhimurium* genetic deletion mutant microorganism.

Poultry suitable for use in the method of invention include chickens, ducks, turkeys, geese, bantams, quail, pheasant, pigeons, or the like, preferably commercially important poultry such as chickens, ducks, geese and turkeys, more preferably chickens and turkeys, particularly preferably chickens.

The *E. coli* genetic deletion mutant microorganism and *S. typhimurium* genetic deletion mutant microorganism may be administered by any conventional means, preferably an economically viable means for the poultry industry such as mass administration via spray or drinking water.

The *E. coli* and *S. typhimurium* genetic deletion mutant microorganisms suitable for use in the method of the invention may be an *E. coli* or *S. typhimurium* microorganism which has been modified by inducing a mutation in a biosynthetic pathway of an amino acid or vitamin or other essential molecule; preferably the mutation affects the biosynthesis of one or more of the amino acids selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine; more preferably by inducing a mutation in an aromatic vitamin biosynthetic pathway; particularly preferably by inducing a mutation in the aropathway, more particularly in the aroA gene. Specific examples of the preferred *E. coli* and *S. typhimurium* genetic deletion mutant microorganisms are those having the identifying characteristics, respectively, of *E. coli* aroA- PTA-5094 and *S. typhimurium* STM-1.

Immunogenically effective amounts suitable for use in the method of the invention may vary according to the age and size of the host, the severity of the infection, the virility of the pathogen, the mode of administration or the like. In general, suitable effective amounts may be that amount of an *E. coli* genetic deletion mutant microorganism sufficient to provide about $10^2$ to $10^{14}$ cfu, preferably about $5.0\times10^2$ to $5.0\times10^{10}$ cfu, more preferably about $3.0\times10^6$ cfu to $6.0\times10^6$ cfu per dosage unit and that amount of a *S. typhimurium* genetic deletion mutant microorganism sufficient to provide about $10^2$ to $10^{14}$ cfu, preferably about $5.0\times10^2$ to $5.0\times10^{10}$ cfu, more preferably about $2.0\times10^6$ cfu to $6.0\times10^6$ cfu per dosage unit.

For a more clear understanding of the invention, the following examples are set forth below. These examples are merely illustrative and are not understood to limit the scope or underlying principles of the invention in any way. Indeed, various modifications of the invention, in addition to those shown and described herein, will become apparent to those skilled in the art from the examples set forth hereinbelow and the foregoing description. Such modifications are also intended to fall within the scope of the appended claims.

EXAMPLE 1

Construction of Aroa Gene Delated *E. Coli* Mutant

I) Recipient

The parental organism is an avian isolate of *E. coli* isolated from a clinical case of avian colibacillosis submitted to the Veterinary Laboratories Agency (VLA), Addlestone, Surrey, UK and serotyped at VLA in 1995. The parent strain was selected for its colonization, invasion, persistence and pathogenicity in one-day-old SPF chicks and by in vitro characterization for its antibiotic sensitivity pattern. The recipient strain was generated by conjugation between the transformed donor (*E. coli* K12 S17 λ pir harboring PNG101 with aroA harboring 100 bp deletion) and wild-type parent strain (wild-type *E. coli* isolate EC34195).

II) Characterization of the Deletion

The aroA gene, which encodes 3-phosphoenolpyruvylshikimate-5-phosphate synthetase, an enzyme of the common aromatic biosynthetic pathway, is located adjacent and promoterdistal to serC in the serC-aroA operon. Loss of function for the aroA gene in the recipient results in a requirement for aromatic metabolites, including tyrosine, phenylalanine, tryptophan, p-aminobenzoate (PABA) and 2,3-dihydroxybenzoate. The requirement for PABA, a metabolite not found in vertebrate tissues, results in attenuation of in vivo growth.

III) Construction of the aroA Deleted *E. coli* Mutant a) PCR primers are designed incorporating SrfI and BglII restriction sites and stop codons to amplify two separate PCR products of approximately 650 bp for the 5' and 3' ends of the aroA gene from the poultry *E. coli* O78 isolate described above.

b) Both PCR products are digested with BglII for 2 hours, electrophoresis is run for 1 hour at 100 volts, the bands are excised and the respective bands are purified using SephaGlas bandprep kit.

c) Equal volumes of each purified PCR product are mixed and ligated into pCR2.1.

d) Ligated plasmid harboring aroA are transformed into DH5α maxi-competent cells and cloning is confirmed by restriction enzyme mapping and PCR.

e) Complete aroA gene with deletion from pCR2.1 is excised with EcorV and SpeI then purified and ligated into a predigested (SpeI) suicide vector (SacB, pKNG101), transformed into competent *E. coli* K12 S17 λ pir and cloning is confirmed by restriction enzyme mapping and PCR.

f) A conjugation is performed between donor (*E. coli* S17 λ pir harboring pKNG101 with aroA harboring 100 bp deletion) and wild-type *E. coli* isolate.

g) Colonies appearing after 48 hours incubation at 37° C. are subcultured onto minimal media supplemented with gentamicin and streptomycin and aromatic amino acids (20 mg/l of each of DL tryptophan, DL phenylalanine and DL tyrosine). Individual colonies are tested by PCR. Colonies that yielded a wild-type PCR product and mutated PCR product of some 100 bp smaller are retained for further studies.

h) Single crossovers are cultured in LB-G broth supplemented with 10% sucrose at 37° C. with gentle agitation for 16 hours. Serial dilutions of the overnight cultures are plated onto LB-G plates supplemented with 10% sucrose and incubated at 37° C. for 16 hours.

i) Colonies which grow on the 10% sucrose LB-G plates are subcultured onto each of LB-G, LB-G+gentamicin and streptomycin and minimal and incubated at 37° C. for 16 hours. Colonies only growing on the LB-G plates (double crossovers) are subcultured onto 5% sheep's blood agar and maintained at 4° C.

IV) Intermediate Cloning Vector

Suicide vector (SacB, PNG101) was the intermediate cloning vector. Conjugation was performed between donor (S17 harboring PNG101 with aroA harboring 100 bp deletion) and wild-type *E. coli* isolate.

EXAMPLE 2

Preparation of Master Seed

The *E. coli* aroA-strain (constructed in Example 1) is grown on tryptic soy agar plate once and passed 3 times in tryptic soy broth. The culture is distributed into glass vials, sealed and lyophilized.

EXAMPLE 3

Evaluation of the Efficacy of a Combination of an *E. coli* Genetic Deletion Mutant Microorganism Plus a *S. typhimurium* Genetic Deletion Mutant Microorganism in Chickens Against *E. coli* and *Salmonella* Infections In this evaluation, the *E. coli* genetic deletion mutant microorganism used is the *E. coli* aroA-strain prepared in Examples 1 and 2 hereinabove and the *S. typhimurium* genetic deletion mutant microorganism used is the *S. typhimurium* STM-1 prepared as described in U.S. Pat. No. 6,231,871 B1.

For this evaluation, 103 SPF white leghorn chickens of mixed gender are divided into 5 groups, 2 groups of 25 each, 2 groups of 24 each and one control (unvaccinated, unchallenged) group of 5. Birds are hand picked and placed in an arbitrarily assigned isolator. Each test group is housed in 2 isolators, each containing 12 to 13 birds.

Test Groups A and B (vaccinates) are vaccinated at one day of age by coarse spray using a hand-held sprayer. At one day of age, birds in each of Test Group A and B are grouped together in a small container and the combined *E. coli* and *S. typhimurium* genetic deletion mutant microorganism vaccine is sprayed to the heads of the birds until the calibrated dosage is given (a target of $5.0 \times 10^6$ cfu *E. coli* aroA-PTA-5094 and a target of $5.0 \times 10^6$ cfu *S. typhimurium* STM-1 per dose of 0.5 mL per bird). Each vaccine, *E. coli* aroA- PTA-5094 and *S. typhimurium* STM-1, is diluted with sterile phosphate buffered saline (PBS) and then mixed together prior to vaccination. At two weeks of age, Test Groups A and B are vaccinated again by the drinking water route. Birds are deprived of drinking water for 3 hours prior to the vaccination via drinking water route. The two vaccines prepared hereinabove for the spray application are added to a measured quantity of cool distilled water to a final titer of $5.0 \times 10^6$ cfu per dose (0.5 mL per bird) for each vaccine. The vaccine-containing water is the sole source of drinking water. Once the vaccine-containing water is consumed, the drinker is removed from the unit and the regular drinking water source is resumed.

At six weeks of age, each bird in Test Group A (vaccinated) and Test Group C (unvaccinated) is challenged via the intratracheal (IT) route with a virulent strain of *E. coli* 078 at a titer of $5.89 \times 10^8$ cfu per dose. Also, at six weeks of age, each bird in Test Group B (vaccinated) and Test Group D (unvaccinated) are challenged by oral gavage with a nalidixic acid resistant strain of *S. typhimurium* at a titer of $4.01 \times 10^6$ cfu per dose.

Test Group E is unvaccinated and unchallenged (negative control group). Vaccinates and control birds are reared in separate isolators until the completion of the study.

All birds are under veterinary care with feed and water available *ad libitum*. Birds are observed daily for 7 days post-challenge. At the end of the 7-day post-challenge period, all surviving birds are necropsied and Groups A and C are examined for the presence of lesions typical of avian colibacillosis. Non-surviving birds and birds that demonstrated any of the grossly visible lesions such as perihepatitis, pericarditis, airsacculitis, cellulitis, or arthritis are considered positive for colibacillosis. The data are shown in Table I.

Groups B and D are examined for colonization by *S. typhimurium* in the organs. The data are shown in Table II.

TABLE I

EVALUATION OF EFFICACY OF A COMBINATION OF *E. COLI* AND *S. TYPHIMURIUM* GENETIC DELETION MUTANT MICROORGANISMS IN CHICKENS AGAINST *E. COLI* 078 INFECTION AND DISEASE*

| Test Group | Vaccination Route | Challenge Route | % Mortality | % Surviving birds with gross lesions | | | | | % Positive for Colibacillosis |
|---|---|---|---|---|---|---|---|---|---|
| | | | | Hep[a] | Card[b] | Air[c] | Cell[d] | Arth[e] | |
| A | Coarse spray | IT | 33.3 | 43.8 | 50.0 | 43.8 | 12.5 | 12.5 | 66.7 |
| C | None | IT | 29.2 | 64.7 | 82.4 | 82.4 | 35.3 | 0 | 87.5 |
| E | None | None | 0 | 0 | 0 | 0 | 0 | 0 | 0 |

[a]Perihepatitis
[b]Pericarditis
[c]Airsacculitis
[d]Cellulitis
[e]Arthritis

*Vaccine is administered to chickens as an aid in the prevention of colibacillosis associated with infection by *E. coli*.

TABLE II

EVALUATION OF EFFICACY OF
A COMBINATION OF *E. COLI* AND *S. TYPHIMURIUM*
GENETIC DELETION MUTANT MICROORGANISMS IN
CHICKENS AGAINST SALMONELLA INFECTION AND DISEASE*

| Test Group | Vaccination Route | Challenge Route | % *S. typhimurium* Positive | | |
|---|---|---|---|---|---|
| | | | Organ Pool | Intestine Pool | Cecal Contents |
| B | Coarse Spray/Drinking water | OG[a] | 32 | 80 | 68 |
| D | None | OG[a] | 68 | 100 | 92 |
| E | None | None | 0 | 0 | 0 |

[a] oral gavage
*Vaccine is administered to chickens as an aid in the reduction of Salmonella colonization of the internal organs, including the intestines and ceca.

As the results of Tables I and II indicate, there is a significant reduction in both colibacillosis associated with *E. coli* infection, and incidence of *Salmonella* infection, as a result of the combination vaccine of the invention. In Table II, there is a large reduction in *Salmonella* colonization, meaning less birds have been infected and are therefore less likely to develop full-blown disease, and are less likely to transmit the disease to their eggs.

What is claimed is:

1. An avian vaccine composition which comprises: an immunogenically effective amount of a combination of an *Escherichia coil* genetic deletion mutant microorganism and a *Salmonella typhimurium* genetic deletion mutant microorganism, wherein the genetic deletion mutants comprise constructed aroA deletion mutations that cause an attenuation of in vivo growth of the *E. coli* and *S. typhimuriumin* in the absence of p-aminobenzoate (PABA), and a pharmacologically acceptable carrier.

2. The composition according to claim 1 wherein said carrier is a balanced salt solution suitable for use in tissue or cell culture media.

3. The composition according to claim 1 wherein said carrier is distilled water.

4. The composition according to claim 1 wherein the immunogenically effective amount is sufficient to provide about $5.0 \times 10^2$ cfu to $5.0 \times 10^{10}$ cfu of said *Escherichia coil* genetic deletion mutant microorganism and about $5.0 \times 10^2$ cfu to $5.0 \times 10^{10}$ cfu of said *Salmonella typhimurium* genetic deletion mutant microorganism.

5. The composition according to claim 1 wherein said *Escherichia coil* genetic deletion mutant is the microorganism deposited with the American Type Culture Collection (ATCC) under assigned Accession Number PTA-5094.

6. The composition according to claim 1 wherein said *Salmonella typhimurium* genetic deletion mutant microorganism is STM-1 deposited with the Australian Government Analytical Laboratories (AGAL) under assigned Accession Number N93/43266.

7. The composition according to claim 6 wherein the *Escherichia coil* genetic deletion mutant is the microorganism deposited with the American Type Culture Collection (ATCC) under assigned Accession Number PTA-5094.

8. The composition according to claim 7 wherein the immunogenically effective amount is an amount sufficient to provide about $3.0 \times 10^6$ to $6.0 \times 10^6$ cfu of *E. coil* aroA- ATCC PTA-5094 and about $2.0 \times 10^6$ to $6.0 \times 10^6$ cfu of *S. typhimurium* STM-1.

9. A method for protecting poultry against disease or infection caused by *E. coil* and *S. typhimurium* which comprises administering to said poultry an immunogenically effective amount of a combination of an *Escherichia coil* genetic deletion mutant microorganism and a *Salmonella typhimurium* genetic deletion mutant microorganism, wherein the genetic deletion mutants comprise constructed aroA deletion mutations that cause an attenuation of in vivo growth of the *E. coli* and *S.typhimuiruim* in the absence of p-aminobenzoate (PABA).

10. The method according to claim 9 wherein the poultry is selected from the group consisting of chickens; ducks; geese; turkeys; bantams; quail; pheasant; and pigeons.

11. The method according to claim 9 wherein said combination is administered via mass application.

12. The method according to claim 9 wherein said *Escherichia coil* genetic deletion mutant is the microorganism deposited with the American Type Culture Collection (ATCC) under assigned Accession Number PTA-5094.

13. The method according to claim 9 wherein said microorganism is STM-1 deposited with the Australian Government Analytical Laboratories (AGAL) under Accession Number N93/43266.

14. The method according to claim 13 wherein said *E. coil* microorganism is the microorganism deposited with the American Type Culture Collection (ATCC) under assigned Accession Number PTA-5094.

15. The method according to claim 14 wherein the immunogenically effective amount is the amount sufficient to provide about $3.0 \times 10^6$ to $6.0 \times 10^6$ cfu of *E. coil* aroA- ATCC PTA-5094 and about $2.0 \times 10^6$ to $6.0 \times 10^6$ cfu of *S. typhimurium* STM-1.

* * * * *

UNITED STATES PATENT AND TRADEMARK OFFICE
CERTIFICATE OF CORRECTION

PATENT NO. : 7,297,338 B2  Page 1 of 1
APPLICATION NO. : 10/837810
DATED : November 20, 2007
INVENTOR(S) : Henry H. Fan et al.

It is certified that error appears in the above-identified patent and that said Letters Patent is hereby corrected as shown below:

In the Claims, please see

| Column | Claim | Line | Change |
|--------|-------|------|--------|
| 9  | 1  | 30 | *coil* to *coli* |
| 9  | 4  | 44 | *coil* to *coli* |
| 9  | 5  | 49 | *coil* to *coli* |
| 10 | 7  | 7  | *coil* to *coli* |
| 10 | 8  | 13 | *coil* to *coli* |
| 10 | 9  | 17 | *coil* to *coli* |
| 10 | 9  | 19 | *coil* to *coli* |
| 10 | 9  | 24 | *S.typhimuiruim* to *S. typhimurium* |
| 10 | 12 | 33 | *coil* to *coli* |
| 10 | 14 | 40 | *coil* to *coli* |
| 10 | 15 | 46 | *coil* to *coli* |

In the Claims, please see

| Column | Claim | Line | Change |
|--------|-------|------|--------|
| 9 | 1 | 34 | *typhimuriumin* to *typhimurium* |

Signed and Sealed this

Twenty-eighth Day of April, 2009

JOHN DOLL
*Acting Director of the United States Patent and Trademark Office*